US007666687B2

(12) United States Patent
Webster et al.

(10) Patent No.: US 7,666,687 B2
(45) **Date of Patent: *Feb. 23, 2010**

(54) MINIATURIZED FLUID DELIVERY AND ANALYSIS SYSTEM

(76) Inventors: James Russell Webster, 195-39, Sec. 4, Chung Hsing Rd., Chutung, Hsinchu 310 (TW); Ping Chang, 195-39, Sec. 4, Chung Hsing Rd., Chutung, Hsinchu 310 (TW); Shaw-Tzuv Wang, 195-39, Sec. 4, Chung Hsing Rd., Chutung, Hsinchu 310 (TW); Chi-Chen Chen, 195-39, Sec. 4, Chung Hsing Rd., Chutung, Hsinchu 310 (TW); Rong-I Hong, 195-39, Sec. 4, Chung Hsing Rd., Chutung, Hsinchu 310 (TW)

( * ) Notice: Subject to any disclaimer, the term of this patent is extended or adjusted under 35 U.S.C. 154(b) by 540 days.

This patent is subject to a terminal disclaimer.

(21) Appl. No.: 11/504,303

(22) Filed: Aug. 15, 2006

(65) Prior Publication Data

US 2007/0031287 A1 Feb. 8, 2007

Related U.S. Application Data

(62) Division of application No. 10/437,046, filed on May 14, 2003, now Pat. No. 7,241,421.

(30) Foreign Application Priority Data

Sep. 27, 2002 (TW) .............................. 91122431 A

(51) Int. Cl.
*G01N 1/10* (2006.01)
*G01N 33/543* (2006.01)

(52) U.S. Cl. ....................... 436/180; 436/518; 436/524; 422/81; 422/100; 422/103; 435/7.1; 435/287.2; 435/287.3; 435/288.4; 435/288.5

(58) Field of Classification Search ................... 436/46, 436/180, 518, 524; 422/81, 100, 103; 435/6, 435/7.1, 287.1, 287.2, 287.3, 288.4, 288.5
See application file for complete search history.

(56) References Cited

U.S. PATENT DOCUMENTS 4,203,848 A 5/1980 Grandine, II
4,908,112 A 3/1990 Pace
4,920,056 A 4/1990 Dasgupta (Continued)

FOREIGN PATENT DOCUMENTS

WO WO 01/62887 A1 8/2001

(Continued)

*Primary Examiner*—Maureen M Wallenhorst
(74) *Attorney, Agent, or Firm*—Alexander Chen, Esq.

(57) ABSTRACT

A method for combining a fluid delivery system with an analysis system for performing immunological or other chemical of biological assays. The method includes a miniature plastic fluidic cartridge containing a reaction chamber with a plurality of immobilized species, a capillary channel, and a pump structure along with an external linear actuator corresponding to the pump structure to provide force for the fluid delivery. The plastic fluidic cartridge can be configured in a variety of ways to affect the performance and complexity of the assay performed.

8 Claims, 3 Drawing Sheets

U.S. PATENT DOCUMENTS 5,585,069 A 12/1996 Zanzucchi et al.
5,632,876 A 5/1997 Zanzucchi et al.
5,644,177 A 7/1997 Guckel et al.
5,660,728 A 8/1997 Saaski et al.
5,681,484 A 10/1997 Zanzucchi et al.
5,819,749 A 10/1998 Lee et al.
5,839,467 A 11/1998 Saaski et al.
5,842,787 A 12/1998 Kopf-Sill et al.
5,856,174 A 1/1999 Lipshutz et al.
5,858,195 A 1/1999 Ramsey
5,858,804 A 1/1999 Zanzucchi et al.
5,869,004 A 2/1999 Parce et al.
5,876,675 A 3/1999 Kennedy
5,882,465 A 3/1999 McReynolds
5,901,939 A 5/1999 Cabuz et al.
5,922,591 A 7/1999 Anderson et al.
5,939,291 A 8/1999 Loewy et al.
5,957,579 A 9/1999 Kopf-Sill et al.
5,958,694 A 9/1999 Nikiforov
5,958,804 A 9/1999 Brown, Jr. et al.
RE36,350 E 10/1999 Swedberg et al.
5,976,336 A 11/1999 Dubrow et al.
5,989,402 A 11/1999 Chow et al.
5,992,769 A 11/1999 Wise et al.
6,001,231 A 12/1999 Kopf-Sill
6,007,690 A 12/1999 Nelson et al.
6,032,923 A 3/2000 Biegelsen et al.
6,033,544 A 3/2000 Demers et al.
6,042,709 A 3/2000 Parce et al.
6,043,080 A 3/2000 Lipshutz et al.
6,048,498 A 4/2000 Kennedy
6,063,589 A 5/2000 Kellogg et al.
6,068,751 A 5/2000 Neukermans
6,068,752 A 5/2000 Dubrow et al.
6,074,725 A 6/2000 Kennedy
6,074,827 A 6/2000 Nelson et al.
6,086,740 A 7/2000 Kennedy
6,086,825 A 7/2000 Sundberg et al.
6,089,534 A 7/2000 Biegelsen et al.
6,090,251 A 7/2000 Sundberg et al.
6,100,541 A 8/2000 Nagle et al.
6,102,068 A 8/2000 Higdon et al.
6,107,044 A 8/2000 Nikiforov
6,120,665 A 9/2000 Chiang et al.
6,123,316 A 9/2000 Biegelsen et al.
6,132,685 A 10/2000 Kercso et al.
6,149,870 A 11/2000 Parce et al.
6,153,073 A 11/2000 Dubrow et al.
6,158,712 A 12/2000 Craig
6,167,910 B1 1/2001 Chow
6,168,948 B1 1/2001 Anderson et al.
6,176,962 B1 1/2001 Soane et al.
6,186,660 B1 2/2001 Kopf-Sill et al.
6,193,471 B1 2/2001 Paul
6,197,595 B1 3/2001 Anderson et al.
6,203,759 B1 3/2001 Pelc et al.
6,213,789 B1 4/2001 Chua et al.
6,224,728 B1 5/2001 Oborny et al.
6,236,491 B1 5/2001 Goodwin-Johansson
6,240,944 B1 6/2001 Ohnstein et al.
6,242,209 B1 6/2001 Ransom et al.
6,255,758 B1 7/2001 Cabuz et al.
6,288,472 B1 9/2001 Cabuz et al.
6,296,020 B1 10/2001 McNeely et al.
6,296,452 B1 10/2001 Caren
6,302,134 B1 10/2001 Kellogg et al.
6,318,970 B1 11/2001 Backhouse
6,322,980 B1 11/2001 Singh
6,326,211 B1 12/2001 Anderson et al.
6,344,326 B1 2/2002 Nelson et al.
6,349,740 B1 2/2002 Cho et al.
6,408,878 B2 * 6/2002 Unger et al. ................ 137/597
6,585,939 B1 7/2003 Dapprich
6,607,907 B2 8/2003 McNeely et al.
6,613,525 B2 9/2003 Nelson et al.
6,613,580 B1 9/2003 Chow et al.
6,613,581 B1 9/2003 Wada et al.
6,616,823 B2 9/2003 Kopf-Sill
6,767,194 B2 * 7/2004 Jeon et al. ................... 417/559
7,186,383 B2 * 3/2007 Webster et al. .............. 422/100
7,241,421 B2 * 7/2007 Webster et al. .............. 422/100
2002/0098097 A1 * 7/2002 Singh ...................... 417/413.1

FOREIGN PATENT DOCUMENTS

WO WO 01/63241 A1 8/2001

* cited by examiner

MINIATURIZED FLUID DELIVERY AND ANALYSIS SYSTEM

CROSS-REFERENCE TO RELATED APPLICATION

This application is a divisional of U.S. patent application Ser. No. 10/437,046, filed May 14, 2003, and now U.S. Pat. No. 7,241,421, issued on Jul. 10, 2007, which is hereby incorporated by reference herein in its entirety.

BACKGROUND OF THE INVENTION

Field of the Invention

This invention relates to a system comprising a fluid delivery and analysis cartridge and an external linear actuator. More particularly, the invention relates to a system for carrying out various processes, including screening, immunological diagnostics, DNA diagnostics, in a miniature fluid delivery and analysis cartridge.

Recently, highly parallel processes have been developed for the analysis of biological substances such as, for example, proteins and DNA. Large numbers of different binding moieties can be immobilized on solid surfaces and interactions between such moieties and other compounds can be measured in a highly parallel fashion. While the sizes of the solid surfaces have been remarkably reduced over recent years and the density of immobilized species has also dramatically increased, typically such assays require a number of liquid handling steps that can be difficult to automate without liquid handling robots or similar apparatuses.

A number of microfluidic platforms have recently been developed to solve such problems in liquid handling, reduce reagent consumptions, and to increase the speed of such processes. Examples of such platforms are described in U.S. Pat. Nos. 5,856,174 and 5,922,591. Such a device was later shown to perform nucleic acid extraction, amplification and hybridization on HIV viral samples as described by Anderson et al, "Microfluidic Biochemical Analysis System", Proceeding of the 1997 International Conference on Solid-State Sensors and Actuators, Tranducers '97, 1997, pp. 477-480. Through the use of pneumatically controlled valves, hydrophobic vents, and differential pressure sources, fluid reagents were manipulated in a miniature fluidic cartridge to perform nucleic acid analysis.

Another example of such a microfluidic platform is described in U.S. Pat. No. 6,063,589 where the use of centripetal force is used to pump liquid samples through a capillary network contained on compact-disc liquid fluidic cartridge. Passive burst valves are used to control fluid motion according to the disc spin speed. Such a platform has been used to perform biological assays as described by Kellog et al, "Centrifugal Microfluidics: Applications," Micro Total Analysis System 2000, Proceedings of the uTas 2000 Symposium, 2000, pp. 239-242. The further use of passive surfaces in such miniature and microfluidic devices has been described in U.S. Pat. No. 6,296,020 for the control of fluid in micro-scale devices.

An alternative to pressure driven liquid handling devices is through the use of electric fields to control liquid and molecule motion. Much work in miniaturized fluid delivery and analysis has been done using these electro-kinetic methods for pumping reagents through a liquid medium and using electrophoretic methods for separating and perform specific assays in such systems. Devices using such methods have been described in U.S. Pat. No. 4,908,112, U.S. Pat. No. 6,033,544, and U.S. Pat. No. 5,858,804.

Other miniaturized liquid handling devices have also been described using electrostatic valve arrays (U.S. Pat. No. 6,240,944), Ferrofluid micropumps (U.S. Pat. No. 6,318,970), and a Fluid Flow regulator (U.S. Pat. No. 5,839,467).

The use of such miniaturized liquid handling devices has the potential to increase assay throughput, reduce reagent consumption, simplify diagnostic instrumentation, and reduce assay costs.

SUMMARY OF THE INVENTION

The system of the invention comprises a plastic fluidic device having at least one reaction chamber connected to pumping structures through capillary channels and external linear actuators. The device comprises two plastic substrates, a top substrate and a bottom substrate containing capillary channel(s), reaction chamber(s), and pump/valve chamber (s)—and a flexible intermediate interlayer between the top and bottom substrate which provides providing a sealing interface for the fluidic structures as well as valve and pump diaphragms. Passive check valve structures are formed in the three layer device by providing a means for a gas or liquid to flow from a channel in the lower substrate to a channel in the upper substrate by the bending of the interlayer diaphragm. Furthermore flow in the opposite direction is controlled by restricting the diaphragm bending motion with the lower substrate. Alternatively check valve structures can be constructed to allow flow from the top substrate to the bottom substrate by flipping the device structure. Pump structures are formed in the device by combining a pump chamber with two check valve structures operating in the same direction. A hole is also constructed in the lower substrate corresponding to the pump chamber. A linear actuator—external to the plastic fluidic device—can then be placed in the hole to bend the pump interlayer diaphragm and therefore provide pumping action to fluids within the device. Such pumping structures are inherently unidirectional.

In one embodiment the above system can be used to perform immunoassays by pumping various reagents from an inlet reservoir, through a reaction chamber containing a plurality of immobilized antibodies or antigens, and finally to an outlet port. In another embodiment the system can be used to perform assays for DNA analysis such as hybridization to DNA probes immobilized in the reaction chamber. In still another embodiment the device can be used to synthesize a series of oligonucleotides within the reaction chamber. While the system of the invention is well suited to perform solid-phase reactions within the reaction chamber and provide the means of distributing various reagents to and from the reaction chamber, it is not intended to be limited to performing solid-phase reactions only.

The system of the invention is also well suited for disposable diagnostic applications. The use of the system can reduce the consumables to only the plastic fluidic cartridge and eliminate any cross contamination issues of using fixed-tipped robotic pipettes common in high-throughput applications.

DETAILED DESCRIPTION OF THE INVENTION

Figure 1A:
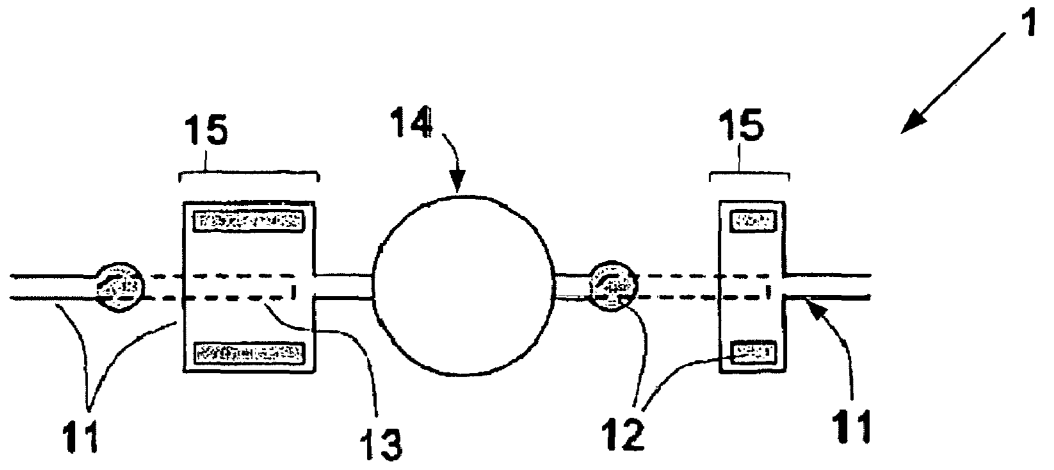
FIG. 1A is a top view of a pump structure within the plastic fluidic device of the invention.
Figure 1B:
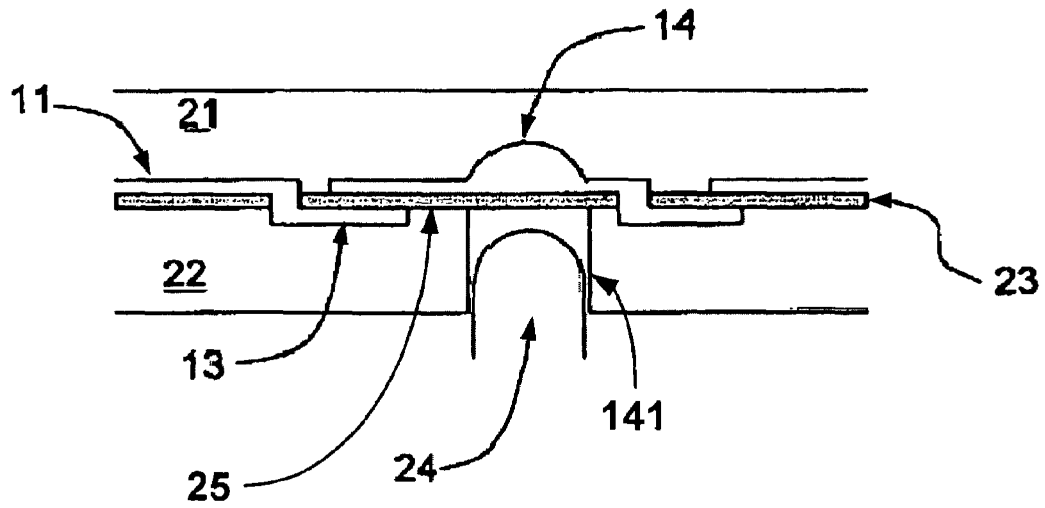
FIG. 1B is a cross section view of the pump structure within the plastic fluidic device of the invention.

The system of the invention comprises a plastic fluidic cartridge and a linear actuator system external to the fluidic cartridge. FIG. 1A shows a cross-sectional view of a pump structure formed within the fluidic cartridge of the invention. The plastic fluidic cartridge comprises three primary layers: an upper substrate 21, a lower substrate 22, and a flexible intermediate interlayer 23, as shown in FIG. 1B. The three layers can be assembled by various plastic assembly methods such as, for example, screw assembly, heat staking, ultrasonic bonding, clamping, or suitable reactive/adhesive bonding methods. The upper and lower substrates, depicted as 21 and 22 in FIG. 1B, both contain a variety of features that define channels of capillary dimensions as well as pump chambers, valve chambers, reaction chambers, reservoirs, and inlet/outlet ports within the cartridge. FIG. 1B shows a top view of the pump structure of FIG. 1A. The pump is defined by a pump chamber 14 and two passive check valves 15 that provide a high resistance to flow in one direction only. Passive check valves 15 comprise a lower substrate channel 13 and an upper substrate channel 11 separated by interlayer 23 such that holes through interlayer 23, depicted as holes 12 in FIG. 1B, are contained within upper substrate channel 11 but not within lower substrate channel 13. Such check valve structures provide a low resistance to a gas/liquid flowing from lower substrate channel 13 to upper substrate channel 11 and likewise provide a high resistance to a gas/liquid flowing from upper substrate channel 11 to lower substrate channel 13. Pump chamber 14 comprises an upper substrate chamber and a hole 141 in lower substrate 22 to free interlayer 23 to act as a diaphragm 25, as depicted in FIG. 1B. A linear actuator 24 external to the fluidic cartridge can then be placed in the hole 131 to bend diaphragm 25 and therefore provide the necessary force to deform the diaphragm.

Figure 2:
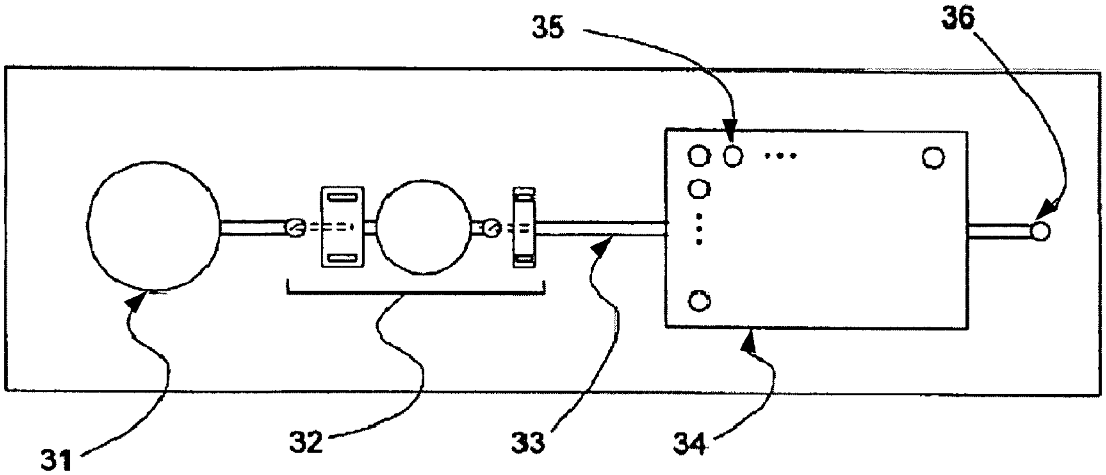
FIG. 2 is a top view of a plastic fluidic device of the invention configured as a single-fluid delivery and analysis device.

FIG. 2 shows a top view of a plastic fluidic cartridge of the invention configured as a single-fluid delivery and analysis device. Fluid is first placed into the reservoir 31 manually or automated using a pipette or similar apparatus. A pump structure 32 similar to that of FIG. 1B is contained within the device. By repeatedly actuating an external linear actuator, fluid in reservoir 31 is pumped through the pump structure 32, the capillary channel 33 and into the reaction chamber 34. Reaction chamber 34 contains a plurality of immobilized bio-molecules 35 for specific solid-phase reactions with said fluid. After a specified reaction time, the fluid is pumped through reaction chamber 34 and out the exit port 36.

Upper substrate 21 and lower substrate 22 of the plastic fluidic cartridge of the invention can be constructed using a variety of plastic materials such as, for example, polymethylmethacrylate (PMMA), polystyrene (PS), polycarbonate (PC), Polypropylene (PP), polyvinylchloride (PVC). In the case of optical characterization of reaction results within a reaction chamber, upper substrate 21 is preferably constructed out of a transparent plastic material. Capillaries, reaction chambers, and pump chambers can be formed in upper substrate 21 and lower substrate 22 using methods such as injection molding, compression molding, hot embossing, or machining. Thicknesses of upper substrate 21 and lower substrate 22 are suitably in, but not limited to, the range of 1 millimeter to 3 millimeter in thickness. Flexible interlayer 23 can be formed by a variety of polymer and rubber materials such as latex, silicone elastomers, polyvinylchloride (PVC), or fluoroelastomers. Methods for forming the features in interlayer 23 include die cutting, rotary die cutting, laser etching, injection molding, and reaction injection molding.

Linear actuator 24 of the present invention, as depicted in FIG. 1B, is preferred to be, but not limited to, an electromagnetic solenoid. Other suitable linear actuators include a motor/cam/piston configuration, a piezoelectric linear actuator, or motor/linear gear configuration.

The invention will further be described in a series of examples that describe different configurations for performing different analyses using the plastic fluidic cartridge and external linear actuator of this invention.

EXAMPLE 1

Immunological Assay

The plastic fluidic cartridge, as shown in FIG. 2, can be utilized to perform immunological assays within reaction chamber 34 by immobilizing a plurality of bio-molecules such as different antibodies 35. In one exemplary embodiment, a sample containing an unknown concentration of a plurality of antigens or antibodies is first placed within reservoir 31. The external linear actuator is then repeatedly actuated to pump the sample from reservoir 31 to reaction chamber 34. The sample is then allowed to react with the immobilized antibodies 35 for a set reaction time. At the end of the set reaction time, the sample is then excluded from reaction chamber 34 through exit port 36. A wash buffer is then placed in reservoir 31 and the external linear actuator is repeatedly actuated to pump the wash buffer through reaction chamber 34 and out the exit port 36. Such wash steps can be repeated as necessary. A solution containing a specific secondary antibody conjugated with a detectable molecule such as a peroxidase enzyme, alkaline phosphatase enzyme, or fluorescent tag is placed into reservoir 31. The secondary antibody solution is then pumped into reaction chamber 34 by repeatedly actuating the linear actuator. After a predetermined reaction time, the solution is pumped out through exit port 36. Reaction chamber 34 is then washed in a similar manner as previously describe. In the case of an enzyme conjugate, a substrate solution is placed into reservoir 31 and pumped into reaction chamber 34. The substrate will then react with any enzyme captured by the previous reactions with the immobilized antibodies 35 providing a detectable signal. For improved assay performance, reaction chamber 34 can be maintained at a constant 37° C.

Figure 3:
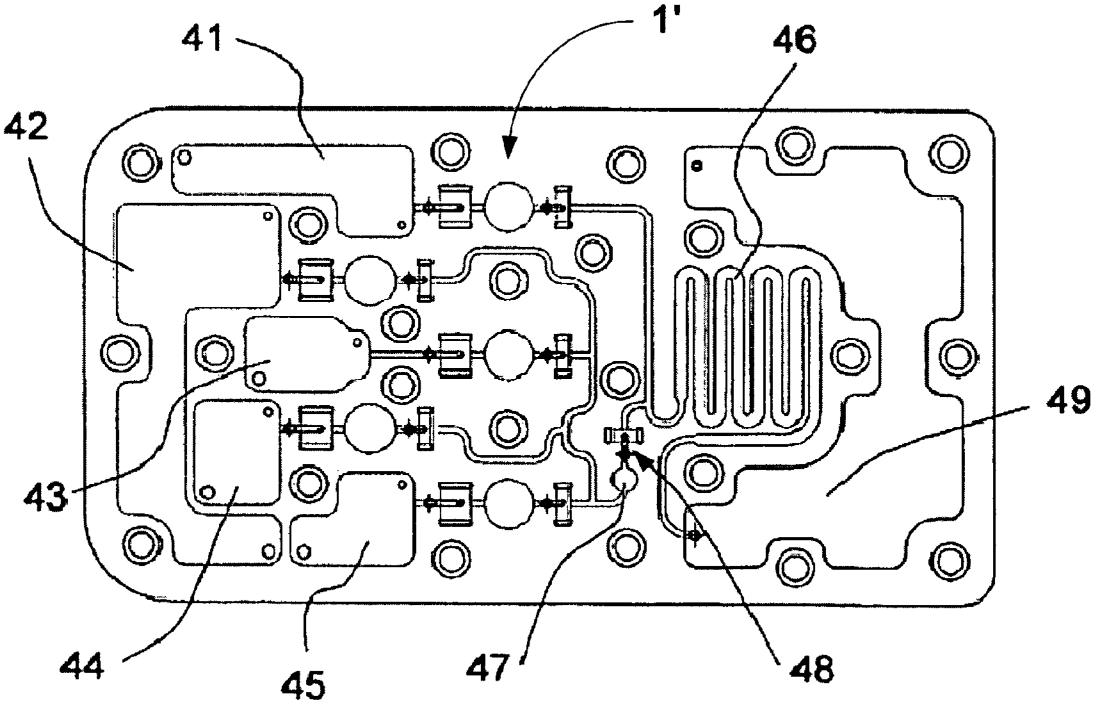
FIG. 3 is a top view of a plastic fluidic device of the invention configured as a 5-fluid delivery and analysis device.

According to the present invention, the plastic fluidic cartridge need not be configured as a single-fluid delivery and analysis device. FIG. 3 shows a plastic cartridge configured as a five fluid delivery and analysis device. Such a device can perform immunological assays, such as competitive immunoassay, immunosorbent immunoassay, immunometric immunoassay, sandwich immunoassay and indirect immunoassay, by providing immobilized antibodies in reaction chamber 46. Here reaction chamber 46 is not configured as a wide rectangular area, but a serpentine channel of dimensions similar to capillary dimension. This configuration provides more uniform flow through the reaction chamber at the expense of wasted space. For example, during immunoassays, a sample containing unknown concentrations of a plurality of antigens or antibodies is placed in reservoir 41. A wash buffer is placed in reservoir 42. Reservoir 43 remains empty to provide air purging. A substrate solution specific to the secondary antibody conjugate is placed in reservoir 44. The secondary antibody conjugate is placed in reservoir 45. Each reservoir is connected to a pump structure 1' similar to that of FIG. 1. Pump structures 1' provide pumping from reservoirs 41, 42, 43, 44, and 45 through reaction chamber 46 to a waste reservoir 49. A secondary reaction chamber 47 is provided for negative control and is isolated from the sample of reservoir 41 by check valve 48. The protocol for performing immunoassays in this device is equivalent to that described previously for the single-fluid configuration with the distinct difference that each separated reagent is contained in a separate reservoir and pumped with a separate pump structure using a separate external linear actuator. First, an external linear actuator corresponding to a pump connected to reservoir 41 is repeatedly actuated until a sample fluid fills reaction chamber 46. After a predetermined reaction time, the sample fluid is pumped to waste reservoir 49 using either a pump connected to sample reservoir 41 or a pump connected to air purge reservoir 43. Next the wash buffer is pumped into reaction chamber 46 by repeatedly actuating the external actuator corresponding to a pump structure connected to wash reservoir 42. The wash and/or air purge cycle can be repeated as necessary. A secondary antibody solution is then pumped into reaction chamber 46 by repeatedly actuating the external linear actuator corresponding to a pump structure connected to reservoir 45. After a predetermined reaction time, the secondary antibody solution is excluded from reaction chamber 46 either by a pump connected to reservoir 45 or a pump connected to air purge reservoir 43. Reaction chamber 46 is then washed as before. The substrate is pumped into reaction chamber 46 by repeatedly actuating a linear actuator corresponding to a pump connected to reservoir 44. After a predetermined reaction time, the substrate is excluded from reaction chamber 46 and replaced with wash buffer from reservoir 42. Results of the immunoassay can then be confirmed by optical measurements through upper substrate 21.

Figure 4:
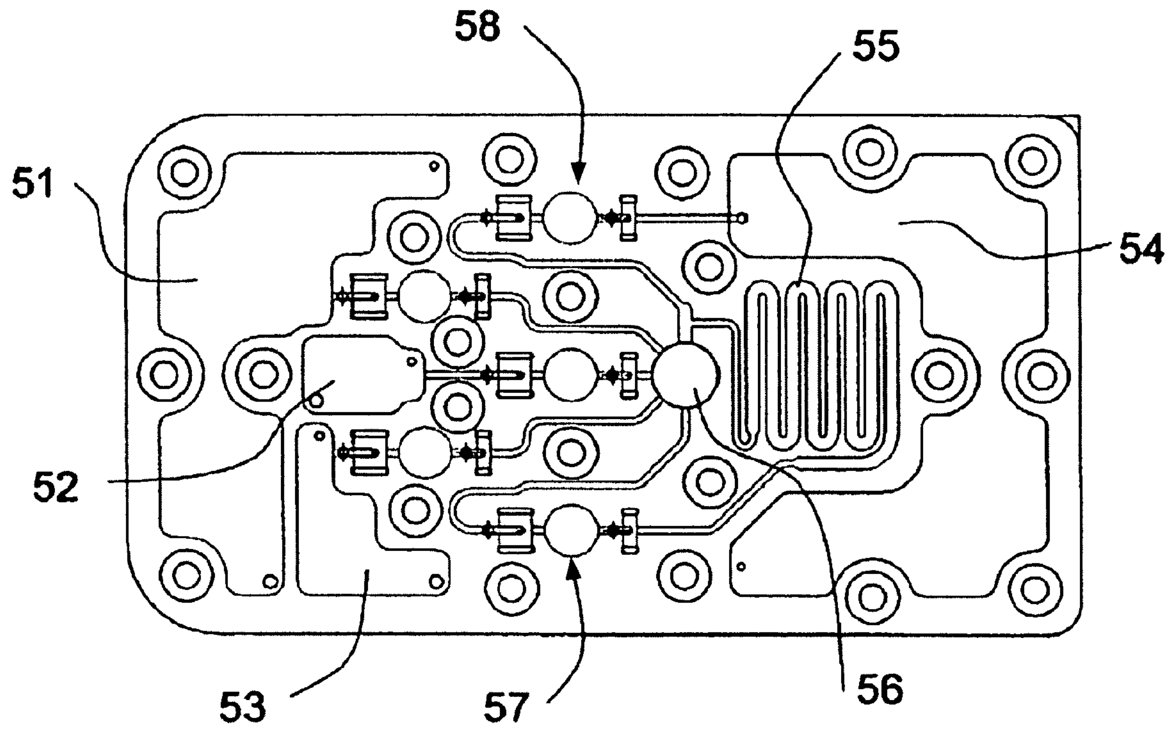
FIG. 4 is a top view of a plastic fluidic device of the invention configured as a re-circulating 3-fluid delivery and analysis device.

Furthermore, the reactions performed with the plastic fluidic cartridge of the invention need not be limited to reactions performed in stationary liquids. FIG. 4 shows a plastic fluidic cartridge according to the invention, configured to provide continuous fluid motion through reaction chamber 55. In this configuration, reservoirs 51, 52, and 53 are connected to separate pump structures similar to those of the five fluid configuration of FIG. 3, but in this case the pump structures are connected to an intermediate circulation reservoir 56. For example, pump structure 57 is connected to circulation reservoir 56 to provide continuous circulation of fluid from circulation reservoir 56 through reaction chamber 55 and returning to circulation reservoir 56. In this manner, a fluid can be circulated through reaction chamber 55 without stopping. Such a fluid motion can provide better mixing, faster reactions times, and complete sample reaction with immobilized species in reaction chamber 55. Pump structure 58 is connected such that it provides pumping of fluids from circulation reservoir 56 to waste reservoir 54. Immunological assays similar to those described above can be performed in this device by immobilizing antibodies in reaction chamber 55 placing the sample containing unknown concentrations of antigens or antibodies in the circulation reservoir 56, placing a solution of secondary antibody conjugate in reservoir 52, placing a substrate solution in reservoir 53, and placing a wash buffer in reservoir 51. The remaining protocol is identical to the above method with the addition of transferring fluids to and from the circulation reservoir 56 and continuously circulating during all reaction times.

EXAMPLE 2

DNA Hybridization

The system of the present invention can also be used to perform DNA hybridization analysis. Using the plastic cartridge of FIG. 4, a plurality of DNA probes are immobilized in reaction chamber 55. A sample containing one or more populations of fluorescently tagged, amplified DNA of unknown sequence is placed in reservoir 52. A first stringency wash buffer is placed in reservoir 51. A second stringency wash buffer is placed in reservoir 53. Reaction chamber 55 is maintained at a constant temperature of 52° C. The sample is transferred to circulation reservoir 56 by repeatedly actuating a linear actuator corresponding to a pump structure connected to reservoir 52. The sample is then circulated through reaction chamber 55 by repeatedly actuating a linear actuator corresponding to pump structure 57. The sample is circulated continuously for a predetermined hybridization time typically from 30 minutes to 2 hours. The sample is then excluded from the circulation reservoir 56 and reaction chamber 55 by actuating pump structures 57 and 58 in opposing fashion. The first stringency wash buffer is then transferred to circulation reservoir 56 by repeatedly actuating the linear actuator corresponding to the pump structure connected to reservoir 51. The first stringency wash buffer is then circulated through reaction chamber 55 in the same manner described above. After a predetermined wash time, the first stringency wash buffer is excluded from reaction chamber 55 and circulation reservoir 56 as described above. A second stringency wash buffer is then transferred to circulation reservoir 56 and circulated through reaction chamber 55 in a manner similar to that previously described. After the second wash buffer is excluded, the DNA hybridization results can be read by fluorescent imaging.

The invention being thus described, it will be obvious that the-invention may be varied in many ways. Such variations are not to be regarded as a departure from the spirit and scope of the invention, and all such modifications as would be obvious to one skilled in the art are intended to be included within the scope of the following claims.

We claim:

1. A method of performing immunological assay of a fluid sample, wherein the method comprises the steps of: (a) pumping said fluid sample from a fluid reservoir, where said fluid sample is placed therein, to a reaction chamber, wherein said fluid reservoir and said reaction chamber are defined in a fluidic cartridge and said reaction chamber comprises therein a plurality of immobilized species; (b) allowing said fluid sample to react with said plurality of immobilized species for a predetermined reaction time; and (c) excluding said fluid sample from said reaction chamber through an exit port wherein said fluid reservoir, said reaction chamber and said exit port are connected by one or more channels of capillary dimensions, wherein said fluidic cartridge includes a first substrate, a second substrate and an flexible intermediate interlayer sealedly interfaced between said first substrate and said second substrate to form therein said fluid reservoir, said one or more channels, said reaction chamber, and said exit port, and wherein said fluidic cartridge further provides a fluid flow controlling structure therein to restrict a flow of said fluid sample through said reaction chamber via said one or more channels in one direction only wherein in said steps (a) and (c), a linear actuator provides a pumping action in a pump chamber defined in said fluidic cartridge so as to pump said fluid sample to flow from said fluid reservoir to said exit port through said reaction chamber and said one or more channels.

2. The method, as recited in claim 1, wherein said pump chamber has a substrate chamber formed in said first substrate and a hole formed in said second substrate to free said flexible intermediate interlayer to act as a pump interlayer diaphragm, wherein said linear actuator moves in said hole to bend said pump interlayer diaphragm and therefore provides a necessary force to deform said pump interlayer diaphragm to provide said pumping action in said pump chamber to pump said fluid sample from said fluid reservoir to flow through said reaction chamber and said one or more channels to said exit port.

3. The method, as recited in claim 2, wherein said fluid flow controlling structure comprises two passive check valves in said fluidic cartridge to restrict said fluid sample to flow from one of said one or more channels in said second substrate to another one of said one or more channels in said first substrate by bending said pump interlayer diaphragm so as to control said fluid sample to only flow from said fluid reservoir to said exit port.

4. The method, as recited in claim 1, wherein said fluid flow controlling structure comprises a first passive check valve positioned before said pump chamber and a second passive check valve positioned after said pump chamber in said fluidic cartridge to provide a lower resistance to said fluid sample to flow from said fluid reservoir to said exit port through said reaction chamber via said one or more channels and a higher resistance to said fluid sample to flow from said exit port to said fluid reservoir.

5. A method of performing immunological assay of a fluid sample, wherein the method comprises the steps of: (a) pumping said fluid sample from a fluid reservoir, where said fluid sample is placed therein, to a reaction chamber, wherein said fluid reservoir and said reaction chamber are defined in a fluidic cartridge and said reaction chamber comprises therein a plurality of immobilized species; (b) allowing said fluid sample to react with said plurality of immobilized species for a predetermined reaction time; and (c) excluding said fluid sample from said reaction chamber through an exit port (d) placing an antibody solution containing a specific secondary antibody conjugated with a detectable molecule into a fluid reservoir; (e) pumping said antibody solution from said fluid reservoir to said reaction chamber; (f) pumping said antibody solution out through an exit port after a predetermined reaction time; and (g) providing a detectable signal, wherein said fluid reservoir, said reaction chamber and said exit port are connected by one or more channels of capillary dimensions, wherein said fluidic cartridge includes a first substrate, a second substrate and an flexible intermediate interlayer sealedly interfaced between said first substrate and said second substrate to form therein said fluid reservoir, said one or more channels, said reaction chamber, and said exit port, and wherein said fluidic cartridge further provides a fluid flow controlling structure therein to restrict a flow of said fluid sample and said antibody solution through said reaction chamber via said one or more channels in one direction only, wherein in said steps (a), (c), (e), and (f), at least one linear actuator provides a pumping action in at least a pump chamber defined in said fluidic cartridge so as to respectively pump said fluid sample and said antibody solution to flow from said fluid reservoir to said exit port through said reaction chamber and said one or more channels.

6. The method, as recited in claim 5, wherein said pump chamber has a substrate chamber formed in said first substrate and a hole formed in said second substrate to free said flexible intermediate interlayer to act as a pump interlayer diaphragm, wherein said at least one linear actuator moves in said hole to bend said pump interlayer diaphragm and therefore provides a necessary force to deform said pump interlayer diaphragm to provide said pumping action in said pump chamber to pump said fluid sample and said antibody solution from said fluid reservoir to flow through said reaction chamber and said one or more channels to said exit port.

7. The method, as recited in claim 6, wherein said fluid flow controlling structure comprises two passive check valves in said fluidic cartridge to restrict said fluid sample and said antibody solution to flow from one of said one or more channels in said second substrate to another one of said one or more channels in said first substrate by bending said pump interlayer diaphragm so as to control said fluid sample and said antibody solution to only flow from said fluid reservoir to said exit port.

8. The method, as recited in claim 5, wherein said fluid flow controlling structure comprises a first passive check valve positioned before said pump chamber and a second passive check valve positioned after said pump chamber in said fluidic cartridge to provide a lower resistance to said fluid sample and said antibody solution to flow from said fluid reservoir to said exit port through said reaction chamber via said one or more channels and a higher resistance to said fluid sample and said antibody solution to flow from said exit port to said fluid reservoir.

* * * * *